(12) United States Patent
Wenstrup

(10) Patent No.: US 6,396,903 B1
(45) Date of Patent: May 28, 2002

(54) REFERENCE GRID FOR SECURITY EQUIPMENT

(76) Inventor: Dakota David Wenstrup, 201 Woodbridge Ct., Easley, SC (US) 29642

( * ) Notice: Subject to any disclaimer, the term of this patent is extended or adjusted under 35 U.S.C. 154(b) by 0 days.

(21) Appl. No.: 09/565,338

(22) Filed: May 5, 2000

(51) Int. Cl.[7] ................................................ G01J 23/10
(52) U.S. Cl. ........................ 378/164; 378/57; 378/195; 378/208
(58) Field of Search ................................ 378/164, 163, 378/57, 51, 195, 208

(56) References Cited

U.S. PATENT DOCUMENTS

| | | | | |
|---|---|---|---|---|
| 3,547,121 A | * | 12/1970 | Cherry | 378/164 |
| 3,639,764 A | * | 2/1972 | Olsen et al. | 378/164 |
| 3,777,643 A | * | 12/1973 | Asbelle et al. | 378/164 |
| 4,020,346 A | * | 4/1977 | Dennis | 378/57 |
| 4,703,566 A | * | 11/1987 | Kwoka | 34/78 |
| 5,052,035 A | * | 9/1991 | Krupnick | 378/163 |
| 5,285,785 A | * | 2/1994 | Meyer | 378/164 |
| 5,974,111 A | * | 10/1999 | Krug et al. | 378/57 |

* cited by examiner

Primary Examiner—Drew A. Dunn

(57) ABSTRACT

A reference grid is incorporated into a flexible transport media for use in internal inspection equipment such as airport x-ray equipment. The reference grid is used as a standard calibration of known density to analyze threat potential of baggage components.

3 Claims, 5 Drawing Sheets

REFERENCE GRID FOR SECURITY EQUIPMENT

FIELD OF THE INVENTION

This invention relates to inspection systems used for determining the content or items of packages or baggage, such as used by airport security systems.

BACKGROUND

Major airports use detection at passenger entry points to check for and identify objects in luggage, bags, packages, or the like. It is an important step in the airport security process to insure that passengers are not carrying objects which could be used in a harmful manner on airplanes.

This equipment in its common form is comprised of a conveyor belt which passes through x-ray equipment. The x-rays are emitted from a source on one side of the traversing baggage and received on the opposite side. A picture of each bag is sent to a screen to be viewed by the security personnel. It is the responsibility of the security personnel to interpret these pictures and identify any potentially harmful metal objects which may be in the baggage.

DETAILED DESCRIPTION

Figure 1:
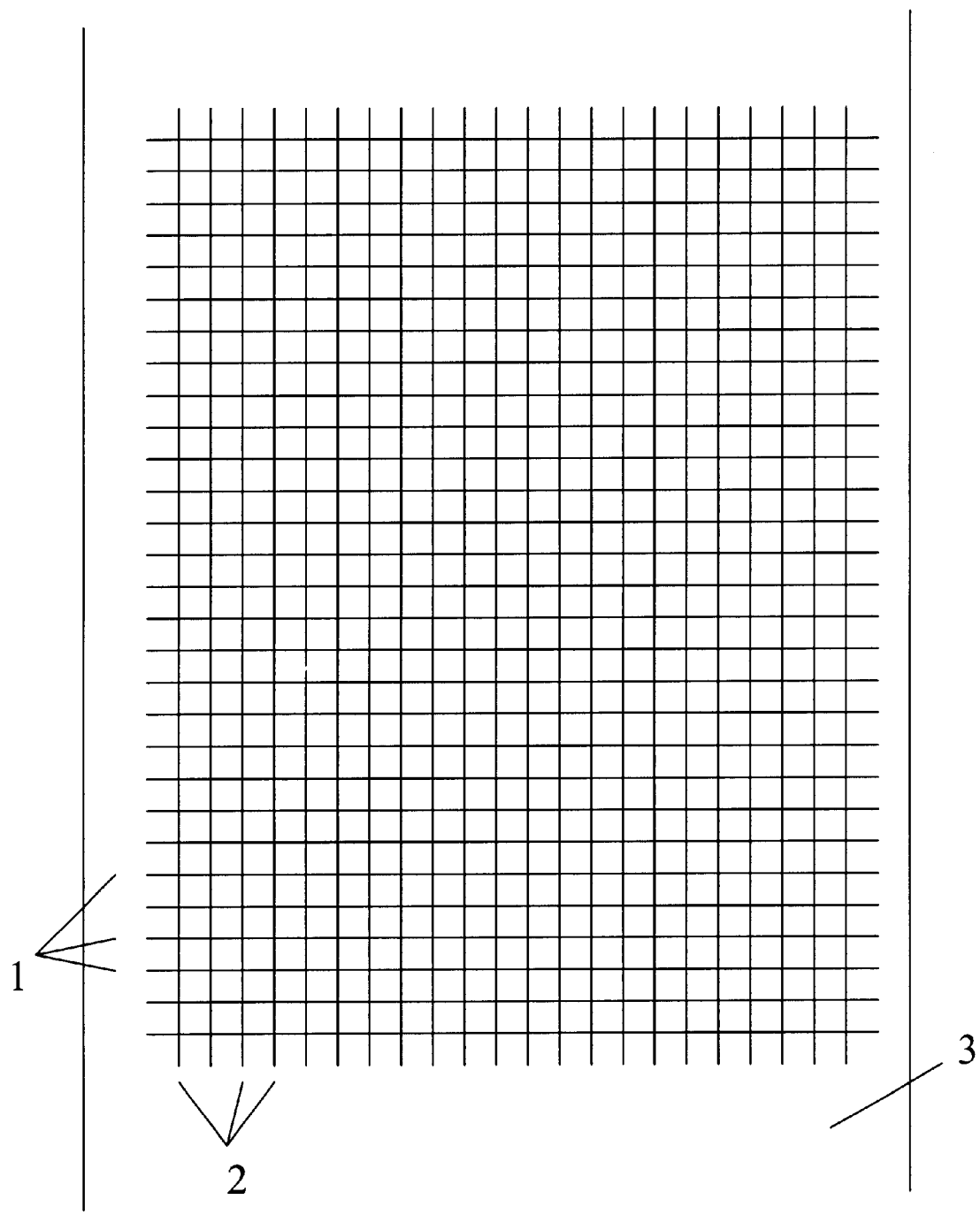
FIG. 1 is an enlarged view of the proposed grid system imposed on a support mechanism.
Figure 5:
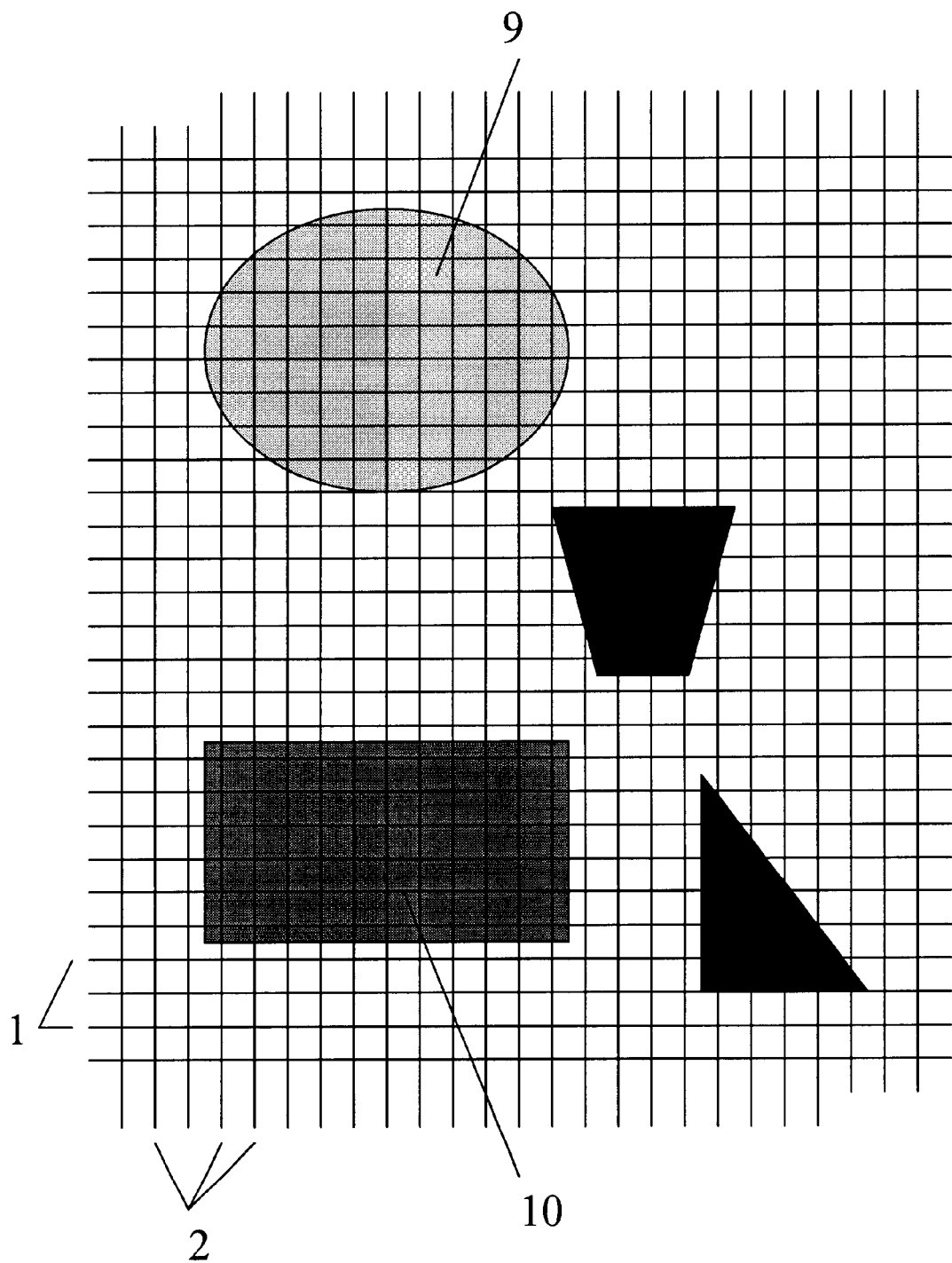
FIG. 5 is a view illustrating the grid system superimposed on several items.

The invention represents a method of superimposing a known grid on the baggage being checked. This grid is a uniform reference to be used in the analysis of the aforementioned piece of baggage. Typically the grid is a metal grid. This grid is uniform in spatial arrangement, as demonstrated in FIG. 1, where 1 represents the reference media running in the width direction, 2 represents the reference media in the length direction, and 3 represents the support media. The grid is also uniform in density so that the security agent has a known reference with which to compare the items displayed in an internal inspection device, typically, the internal inspection device is an x-ray machine. Aberrations to the uniformity of this grid will signal content shielding to the x-ray process whether intentional or unintentional. This is demonstrated in FIG. 5, where object 9 shows a significantly higher degree of contrast between the grid lines 1 and 2 and the object as compared to the contrast in object 10. Variation in the pack density of the baggage and the different contents of the baggage will lead to natural variation in the display of this reference grid.

Superimposition of this known density grid onto the object being investigated also allows numeric and computer analysis of the item. A density map can be drawn of the subject bag and computer analysis of this map can then be used for comparison to stored standards of prohibited articles. This computer analysis can then be used 1) to aid the security personnel in their interpretation of baggage 2) to store density gradient images until flight completion and 3) potentially reduce the number of physical security personnel required.

In one embodiment the invention comprises a metal grid attached to or incorporated within a mat or belt structure upon which the baggage will ride through the x-ray device. Having utilized a consistent density metal wire, tape, thread or other substance in a uniform pattern, the grid pattern will give a uniform reference to the x-ray equipment operator or storage and analysis system.

Figure 2:
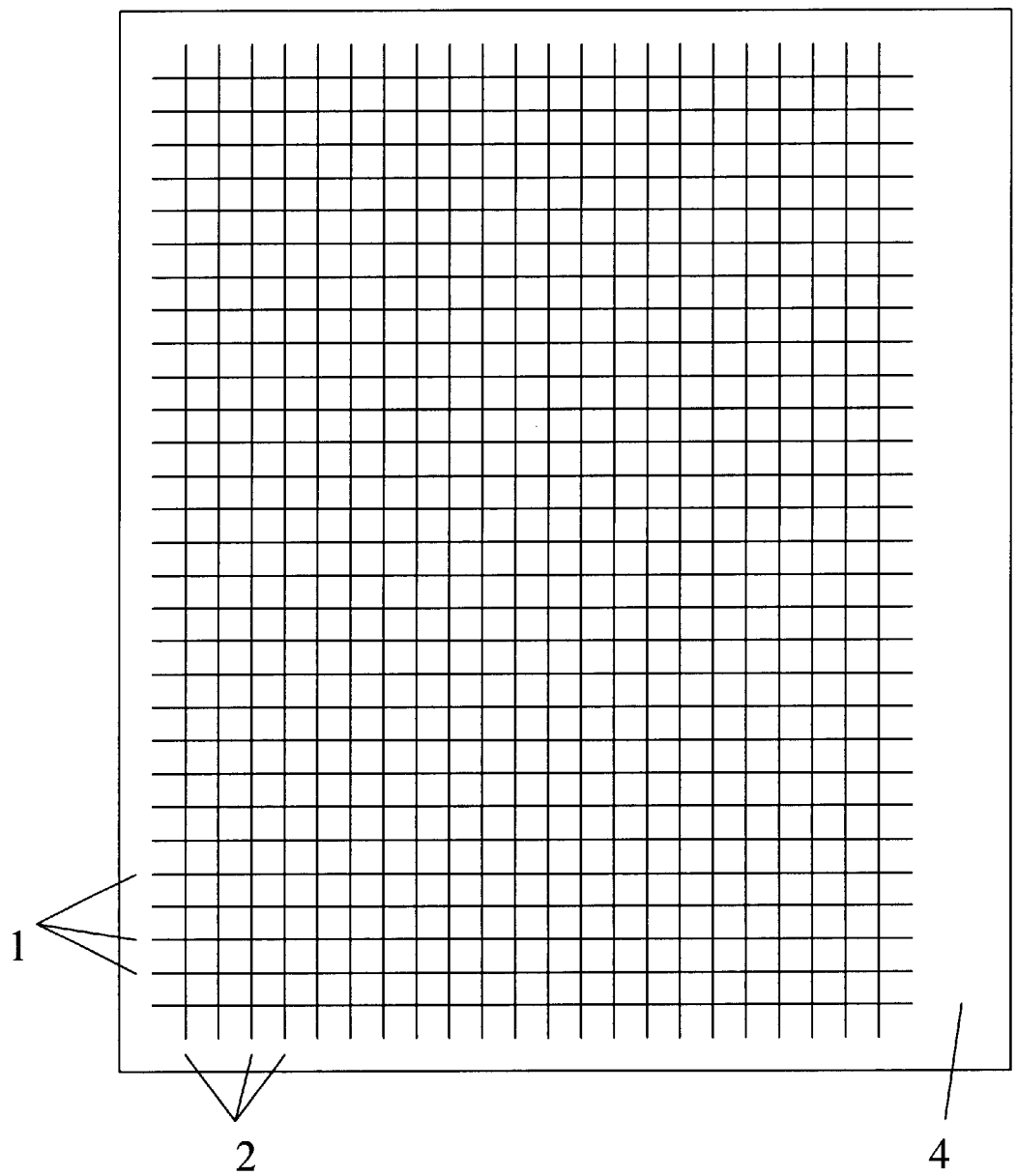
FIG. 2 is a top view of the envisioned device in a mat form.
Figure 3:
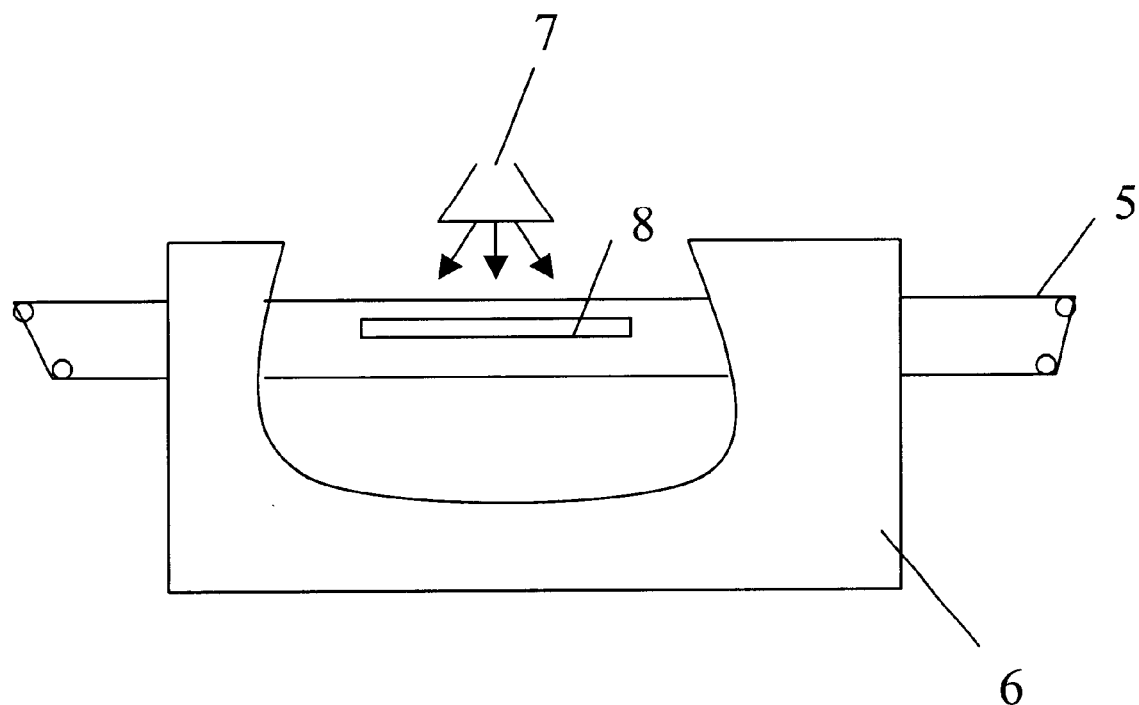
FIG. 3 is a cross sectional view of the envisioned device in a belt form.
Figure 4:
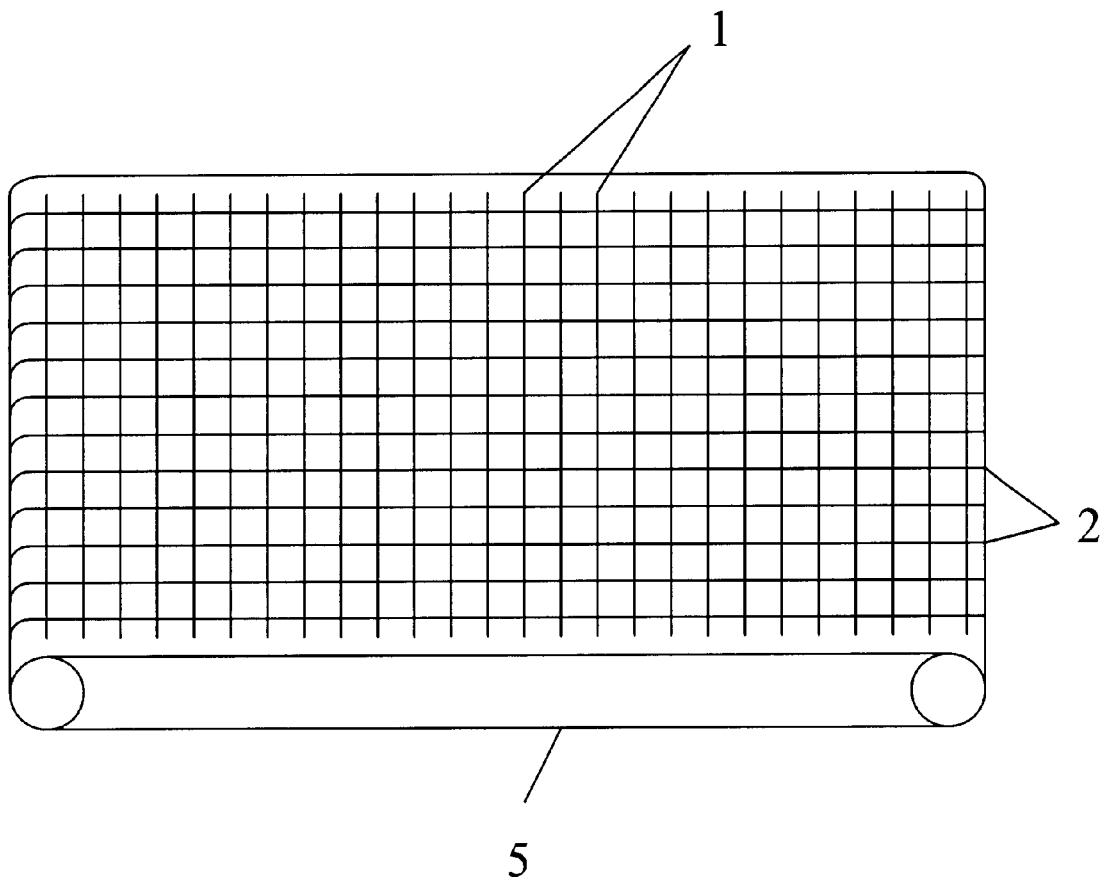
FIG. 4 is a top view of the envisioned device in a belt form.

In a preferred embodiment of the present invention, the grid containing device will be flexible enough to allow incorporation into a belt structure or flexible mat, as shown in FIGS. 2–4, where 4 represents a flexible mat, 5 represents a flexible belt, and 6 represents a typical airport security x-ray machine which includes an x-ray source 7 and an X-ray detection means 8. This will allow continues operation of the equipment in its current construction. Existing x-ray equipment could be converted to include the described reference grid by replacing the belt or attaching the aforementioned mat to the existing belt.

While the grid could be located in a multiplicity of other locations within the x-ray device, the described location is envisioned as the most accurate method of detailing package content density and variations thereof. Additionally the described placement of the grid allows for easy conversion of existing equipment.

I claim:

1. A grid system superimposed on an item for internal inspection of the item with an internal inspection system, wherein the grid system is incorporated into a flexible belt for passage through the internal inspection system.

2. The system of claim 1 wherein the grid system is metal.

3. The system of claim 1 wherein said internal inspection system comprises an x-ray machine.

* * * * *